United States Patent [19]

Ravallo

[11] 4,190,427

[45] Feb. 26, 1980

[54] PLANT CARE COMPOSITION

[75] Inventor: Robert J. Ravallo, Mahopac, N.Y.

[73] Assignee: General Foods Corporation, White Plains, N.Y.

[21] Appl. No.: 793,693

[22] Filed: May 4, 1977

[51] Int. Cl.² .......................... C05B 15/00; C05C 9/00
[52] U.S. Cl. .......................................... 71/29; 71/30; 71/28; 71/64 C
[58] Field of Search .................. 71/11, 28, 13, 29, 30, 71/64 C, 64 E

[56] References Cited

U.S. PATENT DOCUMENTS

| | | | |
|---|---|---|---|
| 3,660,070 | 5/1972 | Maruta | 71/64 E |
| 3,918,952 | 11/1975 | Neumiller | 71/29 |
| 4,001,378 | 1/1977 | Jashoz | 71/28 |

FOREIGN PATENT DOCUMENTS

| | | | |
|---|---|---|---|
| 671553 | 10/1963 | Canada | 71/11 |
| 2448740 | 4/1976 | Fed. Rep. of Germany | 71/11 |

OTHER PUBLICATIONS

*McCutcheon's Detergents and Emulsifiers*, 1975, MC Publshing Co., N. J., p. 69.

Primary Examiner—Morris O. Wolk
Assistant Examiner—Chris P. Konkol
Attorney, Agent, or Firm—Mitchell E. Alter; Daniel J. Donovan; Bruno P. Struzzi

[57] ABSTRACT

Dry foamable concentrates comprising a plant agent, an alpha olefin sulfonate as foaming agent and isopropanol, capable of spumescent constitution with water to provide a stable foam composition acting as a tracer in application.

5 Claims, No Drawings

PLANT CARE COMPOSITION

BACKGROUND OF THE INVENTION

The increased popularity of home gardening, and the expense of commercial servicing has activated interest in homeowner application of plant agents. U.S. Pat. Nos. 3,713,404, 3,871,130 and 3,922,977 of Lavo et al., to the common assignee describe systems and methodology adapted to this interest, the texts of which are incorporated herein by reference. Disclosed is a method for the application of plant agents utilizing a garden hose coupled to a residential water supply providing a stream of water at a static pressure of about 15 to about 70 psig. wherein the stream of water is introduced to a foam generation zone, a foam concentrate comprising a foaming agent and a plant agent is educted into the stream by a venturi arrangement, the mixture is mechanically agitated and the proportion of water and foam concentrate controlled to maintain a dilution of 15 to 90 parts by volume of water to each part of concentrate, and the thus formed foam providing solution is then directed against a foraminous barrier through which a current of air is simultaneously and unidirectionally forced, whereupon the solution is spumed for application into a deformable foam.

The foam concentrates heretofore employed in generating the aforesaid foams are conveniently provided in ready-to-use form as liquid concentrates containing the plant treating agent together with the foaming and stabilizing agents. Such liquid concentrates, however, suffer from lack of stability upon long term storage with solid ingredients, usually organic nitrogen sources, such as urea-formaldehyde, separating in cake form which is difficult to redistribute through the liquid medium. Further, the ability of such concentrates to form spumescent foams diminishes with long term storage, in part due to an increase in viscosity of the concentrates. U.S. Pat. No. 3,918,952 describes such systems, employing alkyl sulfate surfactants.

Accordingly, shelf-stable 'dry' concentrates in ready-to-use form for the purpose of foam application are desired.

It is preferred, however, concentrates may be based upon any lower alkanol, but isopropyl alcohol is preferred for reasons of economy and convenience. Heretofore, it was believed that such systems would afford unsuitable foaming upon storage, and this is consistently the case at reasonable alcohol levels with the broad class of surfactant materials.

However, it has now been discovered that a unique combination of foaming agent and alcohol is singularly effective in dry systems and for use to provide plant agent foams even after substantial storage. The combination is effective even at the low alcohol concentrations desirable for dry storage. Most importantly, it is operable in concentrates having high salt content and/or high insolubles, such as characterize nitrogenous fertilizers.

Foaming systems in accordance with this invention consist essentially of isopropyl alcohol and an alpha olefin sulfonate. The alpha olefin is predominantly long chain comprising at least 8 and preferably at least 12 carbon atoms. Also provided are concentrates embodying foaming agent and at least one plant agent, particularly a particulate material such as a conventional fertilizer of the urea type where the alcohol constitutes less than 15 percent by weight of the composition. Most preferably, the base concentrates are devoid of significant liquid content i.e., are substantially 'dry' but liquifiable in aqueous systems to a reconstituted form, subsequently diluted and foamed for use.

The present new compositions are also particularly well-suited for production of foams which are characterized by a disrupted or discontinuous form as projected or applied. The production of such foams and the apparatus therefore are more fully described in commonly assigned Appln. Ser. Nos. 793,694 and 793,802 of Pitchon, Colton, Kemprowski and Schulman and Colton, Pitchon and Ravallo, respectively, filed concurrently herewith and incorporated herein by reference.

Combined alcohol/foaming agent systems for foaming plant agent compositions are not new, as Lavo et al., U.S. Pat. No. 3,713,404 demonstrates. However, the known isopropyl alcohol based systems exhibit markedly reduced foamability unless the alcohol is utilized in such proportion as to render the desired storage in dry form impractical to impossible. The present discovery provides an isopropyl alcohol based system capable of dry storage and reconstitution with water to acceptable foams. The phenomenon is not general, as many foaming agents, even those which are normally solid, have failed to provide satisfactory foam in combination with isopropyl alcohol. Surprisingly, the alpha olefin sulfonate surfactants were deemed ineffective in U.S. Pat. No. 3,918,952, in liquid systems, and Table 1 at page 17 thereof shows that other surfactants were ineffective in the practice of this invention, emphasizing the selectivity for this system.

This invention concerns itself principally with the provision of dry concentrate formulations capable of reconstitution by liquidification i.e., solution or dispersion in a liquid system in concentrated form which is then diluted in suitable proportion in a foam generator. It is accordingly essential that the concentrate formulation comprise initially a minimum proportion of liquid fraction or deliquescent material such that after storage over a substantial period e.g., in excess of 6 months, the material retains flowability i.e., it may be poured as sand or handled like flour. In order to effect the reformulation with water into a liquid system which upon dilution is capable of substantial foaming in use an alcohol is employed in combination with a foaming agent but must be employed in minimal proportion i.e., not more than about 15% by weight and preferably less than 10% e.g., 3–5% by weight of the composition.

When the alcohol is isopropyl alcohol and the proportions are controlled within the limits described, it has proven essential to employ a solid foaming agent comprising a sulfonate based upon a long chain alpha olefin preferably $C_{12}$–$C_{18}$. Most preferably, the sulfonate is supplied as an alkali metal salt comprising a mixture of about 2 parts by weight of $C_{14}$ to 1 part by weight of $C_{16}$ sulfonate. A suitable example is the 'high active' Bio Terge AS-90F, available commercially from Stepan Chemical Co. Other long chain alpha olefin sulfonate salts are of course suitable, and may be selected with reference to their equivalent foaming power.

The dry concentrate may of course be preformed for use as a liquid concentrate wherein the liquid vehicle comprises an aqueous or oil base system as may be dictated or rendered convenient by the operation in question and the nature of chemical constitutents included within the plant agent compositions which are used therewith.

In accordance with a preferred embodiment of the invention, the dry concentrate comprises a plant nutrient e.g., a fertilizer, often of poor solubility. Controlled release fertilizers typified by low solubility or high particulate content include the urea-aldehyde condensation products, such as urea-formaldehyde, urea-isobutyraldehyde, urea-acetaldehyde, urea-furfural, urea-glyoxal, and urea-crotonaldehyde; ammoniated coal; urea-pyrolyzate; ammonium polyphosphates; and salts such as metal ammonium phosphates and polyphosphates e.g., an alkali metal tripolyphosphate. The concentrates accordingly may comprise a significant proportion ranging up to 20 or 25% by weight of insoluble or difficulty soluble material, in the form of discrete particles or small clumps thereof, which may not be entirely dispersed even with substantial mixing. Ordinarily the system is shaken or mechanically agitated for a brief period e.g., about 30 seconds, to form the concentrated solution, suspension or dispersion of foam generating constituents and the material or materials intended for treatment.

Since the intended use of the spumed foam product is that of a vehicle for applying agents to plants and associated soils, the pH of the applied foam is established at a level which is compatible to plant life, and preferably that level which furthers healthy growth of the plant on which it is deposited. This criterion in general requires the foam to have a pH value of above 6.0 and preferably to be in the range of 6.5 to 9.0. Those versed in the art of horticulture, however, will readily recognize that foams having a slightly lower pH value can be used on "acid-loving" plants such as azaleas and foams having a higher pH level are compatible with other types of plant life.

The foam-providing concentrate of the invention is desirably spumable in an aqueous dispersion to a foam having a controllable degree of expansion when mechanically generated with a flow of tap water from a supply source with a relatively low pressure of 15 lbs. per sq. in. as well as with much higher pressures—typically up to 70 lbs. per sq. in. With respect to obtaining and controlling the degree of expansion of the generated foam under the limiting conditions of homeowner use it may be convenient to employ certain "foam booster" chemical agents in addition to the principal foaming agent such as alkylol ether sulfates, lauric acid monoethanolamide, stearic acid monoethanolamide, lauric acid isopropanolamide and mixtures of lauric acid and myristic acid monoethanolamide, which, of course, will be restricted to materials in the solid state for dry concentrate formation.

In addition to the above, the spumable foam exhibits a degree of stability which precludes the foam from rapidly "breaking", but assures a suitable degree of cohesiveness i.e., providing a visible three-dimensional foam structure on the ground for a period ranging upwards from 5–30 minutes after application. The stability of the foam products of the invention can be controlled where required by the addition of a small amount of certain compounds which are generally classed as humectants. Particularly, polyhydric alcohols such as glycerol, propylene glycol, and ethylene glycol, lauryl alcohol, myristyl alcohol, stearyl alcohol or mixtures thereof have been found to be effective.

As stated above, the foam-providing concentrate comprises a plant agent or combination of agents selected from the general classes of seeds, organic fertilizers, inorganic fertilizers, herbicides, insecticides, fungicides, and sterilants. In almost all instances, with the exception of plant seeds, the plant agent is either soluble in the aqueous concentrate or forms a relatively stable colloidal suspension. In those instances wherein the plant agent is oil soluble, micellar solubilization of the oil soluble plant agent is achieved provided the oil is present in amounts less than about 10 percent by volume of the concentrate. In those instances where the oil content is greater than about 10 percent, an augmenting emulsifier is employed, when necessary, to provide a stable foam-providing emulsion concentrate of the plant agent. Representative auxiliary emulsifiers for this purpose are sodium stearate, sodium laurate, and lauryl benzene sulfonate.

In the preparation of the present concentrates it is advantageous to incorporate dispersants, particularly in the dry concentrates, to prevent caking. Solid dipersants for this purpose are well-known and include, for example, silicon dioxide, pyrogenic silicon dioxide, pyrogenic aluminum oxide, sodium silicoaluminate, and others. Usually such dispersants are employed at low levels, e.g., about 0.5 to about 1.5% by weight of the concentrate. Cab-O-Sil M-5 is a preferred additive.

The amount of the alcohol used in the present concentrates can be varied appreciably to attain desired results correlated to the type of foam produced. Generally, these alcohols can be used at levels ranging from about 1% to about 15% of the concentrate weight, commonly, the level employed is from about 2 to 10%, preferably 5% to about 8%, so that the concentrate assumes a consistency between flour and sand: like buckwheat pancake mix in appearance.

Typically, fertilizer concentrates constituting a preferred embodiment will comprise as much as 75 to 85 percent by weight of nitrogenous material, often urea based and commonly containing a porportion, 25 to 50 percent in some cases, of insoluble or difficultly soluble material. An amount of alcohol/foaming agent in the range of 5 to 15 percent by weight of the dry composition has proven suitable, in a weight proportion conveniently approximating 0.1:1 to 6:1, preferably 1.75:1 to 2.25:1. Fertilizer compositions prepared in accordance with the most preferred aspects of the invention may comprise 0.25 to 2.0 parts of Bio Terge AS-90F and 0.35 to 1.5 parts isopropyl alcohol in combination with about 2 to 30 parts of controlled release fertilizer components. Most preferably, the fertilizer concentrate comprises 1.2 to 14.3 parts of Uramite (M), 0.85 to 10.2 parts of urea (agriculture grade, uncoated prills) and 2 to 2.6 parts of potassium tripolyphosphate as the controlled release composition. Commonly, 0.09 to 0.9 parts of silicon dioxide (Cab-O-Sil) is added as a dispersing aid.

The dry, particulate ingredients used for preparing the present new concentrates are preferably milled or comminuted into fine power form using standard comminuting apparatus, e.g. a Fitz Mill Model D Comminuting Machine, using for example a 50—mesh screen. The comminuted ingredients are thoroughly blended with the foaming agent and the selected alcohol and the resulting uniform mix is then packaged. When water is included, the concentrate is, of course, a liquid and is stored in suitable containers. When the concentrate is dry, which is the preferred form of the invention, the mixture is packaged in dry, sealed containers.

The dry concentrates are constituted with water to obtain liquid concentrates for use with standard foam-producing apparatus. The procedure merely requires mixing the dry concentrate with water, e.g., usually about 3.5 pounds per liter of water, and thoroughly mixing for about 30 seconds during which the ingredients disperse throughout the water. The liquid concentrate is then ready to be used with the foam-producing apparatus.

The diluent used to form the concentrate may comprise a liquid corresponding to the projecting stream e.g. water, or where the plant chemical is oil soluble, the formulation comprehends an emulsifiable concentrate. Whether the starting material is dry or premixed in aqueous or emulsifiable form, the concentrate comprising plant agent and foam generating constituents is ultimately disposed for use in a zone adjacent the point of eduction into the liquid stream, conveniently in a liquid receptacle or tank adapted to form or be carried in a back pack.

In the operation of the system the rate of supply of the projecting fluid is established by an orifice of controllable dimension and the degree of dilution is similarly determined by the selection of concentrate control orifice. The premix or concentrate is educted through a venturi arrangement into the liquid stream established through the foam generation zone, at a suitable rate of dilution, and the thus formed foam providing solution or dispersion is passed through an extended zone for further interaction between plant agent and diluent involving mixing, solvation, surface wetting or other phenomena. The stream is then formed into a projecting spray of incipient foam-forming character by passage through a nozzle as described. The foaming spray is projected through a spaced foraminous barrier and the foam applied to the surface being treated.

As discussed further hereinbelow, in order to produce a satisfactory foam for the purposes of this invention, it must be visible over a short distance, self-coherent and resistant to immediate degradation such that a homeowner traversing a segment of lawn, for example, is able to perceive the limits of the area already covered when making a second pass with the applicator.

The system can take the form of a back pack unit constituting a liquid receptacle for the concentrate connected by means of an eduction tube disposed in operation below the surface of the liquid to a separate foam generation zone defined within the pack, said zone being adapted to receive at the entry a common garden hose and connecting at the outlet side to an enclosed mixing zone formed of a short length of hosing which receives the diluted concentrate, introduced intermediate of the foam generation zone through the eduction tube by means of a venturi arrangement. The nozzle and foraminous barrier elements are contained in a lightweight arc shaped applicator equipped with a handle and suitable controls and the foam is projected therefrom over and about the treated surface in a generally vertical spray i.e. the long dimension of the nozzle orifice and the screen are positioned fixedly relative to the handle such that normal application would dispose them vertically to the ground. The generally F-shaped spray may project 5 to 20 feet, with a relatively even distribution of foam balls formed therein being dispersed freely about the treated surface in a manner controlled by the sweep of the applicator. With some limited experience and information regarding dosage level required, the homeowner can readily direct the spray controllably, and if desired, utilize the foam balls as markers, a few inches or more apart.

The 'foams' of this invention are of restricted durability i.e. are resistant to immediate degradation and of sufficient cohesiveness to permit visual differentiation under normal conditions for periods of at least 5 to 30 minutes, but gradually degrade below the noticeable level over the short term i.e. within 1–2 hours. In other respects, the foams are deformable rather than stiff or resistant to the touch as would characterize a set, hardened or cured foam, and of sufficient surface stickiness to resist removal from the surface to which it is applied by light breezes. Reference to a disrupted foam herein is to be distinguished from the condition referred to as a broken foam, the latter denoting a degradation or breakdown of the ultimate foam structure rather than a stable static condition involving discrete foam formations intended by the former. The foam balls to which reference is made are believed to be made up of a multiplicity of individually foamed particles comprising the usually bubbled configuration cohesively structured into the three dimensional orbs i.e. spheres or domes seen upon projection and application.

These foams may exhibit an expansion ratio of 2:1 up to 200:1 but preferably are of intermediate scale, being of the order of 8:1 up to 80:1. The water powered foam generator will dilute the concentrate with about 15 to 90 preferably 20 to 50 parts by volume of water to one part of concentrate (to provide 0.0002 to 0.003 parts by weight of foam agent as applied). Coverage for such a system will be about 2500 $ft.^2$ in less than 5 minutes at a water rate of 4.75 gpm.

An acceptable expansion ratio may be determined visually with some experience, but initially may be ascertained by reference to the following test: A foam applicator, positioned about 48 inches from the substrate and elevated about a foot above the eduction point is utilized to project foam onto a measured surface (for convenience, one or more three liter beakers provide suitable means for capturing the foam in a measurable manner.) The measured quantity of foam (in case of beakers, filled to the top) is allowed to lie at rest for 5 to 10 minutes, the water drained or otherwise separated in a measured manner and the expansion ratio calculated as follows:

$$\text{Expansion Ratio} = \frac{\text{foam volume}}{\text{water volume}} = \frac{\text{Total volume} - \text{water volume}}{\text{water volume}}$$

Measurements are made with tap water between 50° and 75° F., at flow rates of 4.1 gal/min to 2.75 gal/min.

The term plant is used in its normally broad sense as inclusive of bushes, flowers, shrubs, foliage, trees, grass etc. although it is understood that mechanical application in accordance herewith is of the short throw variety ordinarily connected with ground application.

Those agents which can be applied by the methods of the invention, in addition to seeds, include but are not limited to, organic and inorganic fertilizers, herbicides, fungicides, insecticides, pesticides, sterilants, minerals, hormones and like materials commonly used in agriculture for the maintenance or nurture of plant life, or the control or eradication of pests or disease therein, or the presence of undesired species thereabout.

The following Examples are offered by way of illustration of the various aspects of the present invention, without limitation. All parts are by weight.

EXAMPLE I

A. Identical formulations of a fertilizer base plant agent composition were prepared comprising 1085 parts of Uramite M (a urea-formaldehyde fertilizer manufactured by E. I. du Pont de Nemours & Co.) 772 parts of urea, 300 parts of KTP (Potassium polyphosphate) and 40 parts of ferrous sulfate ($FeSO_4$) by passing the ingredients through a Fitz Mill (Mode D) comminuting device fitted with a 50 mesh screen using hammer blades at a blade speed of 4023 rpm and a motor speed of 1760 rpm. The plant agent composition was then mixed dry with a series of foaming agents as indicated below, by tumbling in a large poly bag until completely blended. The resulting dry, uniform mix is then passed through a 16 mesh screen to remove any residual gross clumping. The resultant concentrates were liquified by addition of 1959 parts of water and shaking for about 30 seconds then diluted in a foam generator of the type described in co-pending and commonly assigned Appln. Ser. Nos. 793,693 and 793,694 of Ravallo and Colton, Pitchon and Ravallo, respectively, filed concurrently herewith, and expressed onto a plot of ground.

TABLE I

Plant Agent Composition 2197 parts
Foaming Agent, parts

|   |   |   |   |   |   |
|---|---|---|---|---|---|
| I Nacconol 90F (linear alkyl sulfonate: Allied Chemical Corp.) | 84 |   |   |   |   |
| II Bio Terge AS-90F (sodium alpha olefin sulfonate:Stepan Chem. Co. |   | 87 |   |   |   |
| III Lathanol LAL (sodium lauryl sulfoacetate: Allied Chem. Corp.) |   |   | 109 |   |   |
| IV Pluronic F68 (polyoxyalkylene derivatives of propylene glycol: Wyandotte Chem. Corp.) |   |   |   | 112 |   |
| V Nacconol 40F (linear alkyl sulfonate:Allied Chem. Corp.) |   |   |   |   | 190 |
| % Foaming Agent/Composition | 3.8% | 4% | 5% | 5% | 8.6% |

In each case, the foam generator provided a dirty liquid to a white froth but in no case was acceptable foam production evidenced, despite the use of different foaming agents over a range of 3.8 to 8.6% by weight of the plant agent composition.

B. In a further trial, 1680 parts of water were added to a formulation comprising 220 parts of isopropyl alcohol and 115 parts of Bio-Terge AS-90F. Unlike the preceding runs, excellent foam was produced. This result was repeated successfully utilizing a dry formulation comprising solid surfactant and IPA which was allowed to stand for a 24 hour period before water was added. The material redispersed readily and produced excellent foam without clogging the gun.

Various modifications on this procedure demonstrate that the effect is not critically dependent upon dilution level or component ratios within the limits of operability for such systems generally.

C. Similar additions of 220 parts of isopropyl alcohol were made to the plant agent composition employing the remaining foaming agents (I and III–V) as in part A above, but without effecting any meaningful improvement in the quantity or quality of foam produced although the ratio of alcohol to foaming agent ranged from 1.15:1 to 2.53:1 at a constant 10 percent based upon plant agent.

EXAMPLE II

Example I (B) is repeated with identical results, utilizing a high active drum dried biodegradable sodium alpha olefin sulfonate based upon a 2:1 blend of $C_{14}$ (1-tetradecene) and $C_{16}$ (1-hexadecene) fractions having a minimum active organic content of 85% with the balance consisting of sodium sulfate, sodium chloride and minor amounts of free oil and volatile matter. Reference to "high active" foaming agent herein refers to foaming power as measured by the Ross-Miles method at 25° C. wherein the minimum standard is reflected in the following Table.

TABLE II

Foaming Power (Ross-Miles Method) at 25° C.

| | Foam Weight, mm. | |
|---|---|---|
| Concentration, % | Distilled Water | 300 ppm |
| 0.05 | 175/170* | 165/165 |
| 0.10 | 185/185 | 180/180 |
| 0.20 | 195/195 | 200/200 |

*Immediate/after 5 minutes

The 'dry' concentrates of the present invention are essentially particulate, or granular in nature, and are flowable in the manner of sand or a flour base material. Although some moisture may be entrained or retained in other manner as by the hygroscopicity of the ingredients, the concentrates are in no sense liquidified, and remain pourable i.e. unclumped under closed storage conditions (sealed without special precaution in ambient air) over extended periods of at least one calendar year. A certain liquid content as, for example, the alcohol is present but the aforementioned characteristics retained, as a further function of the selective use of this material.

I claim:

1. An essentially anhydrous composition adapted for dispersion in a foamed state for treatment of vegetation or terrain comprising:
   a. urea, urea-formaldehyde, potassium tripolyphosphate, and
   b. an isopropyl alcohol and,
   c. an effective amount of a long chain alpha olefin sulfonate containing at least 8 carbon atoms as a foam agent.

2. The composition of claim 1 wherein the long chain alpha olefin sulfonate comprises at least 12 carbon atoms.

3. The composition of claim 2 wherein said alcohol is present in an amount not substantially in excess of 15 percent by weight of said plant agent.

4. The composition of claim 3 wherein the weight ratio of alcohol to sulfonate is between about 1.75:1 and 2.25:1, and said alcohol and sulfonate together do not exceed 15 percent by weight of the composition.

5. The composition of claim 4 wherein said sulfonate constitutes a mixture of 2 parts of sodium ($C_{14}$) sulfonate and 1 part of sodium ($C_{16}$) sulfonate.

* * * * *